(12) United States Patent
Mandrusov et al.

(10) Patent No.: US 7,854,944 B2
(45) Date of Patent: Dec. 21, 2010

(54) TISSUE REGENERATION

(75) Inventors: Evgenia Mandrusov, Campbell, CA (US); Charles Claude, San Jose, CA (US); Eugene T. Michal, San Francisco, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 671 days.

(21) Appl. No.: 11/016,017

(22) Filed: Dec. 17, 2004

(65) Prior Publication Data

US 2006/0134070 A1 Jun. 22, 2006

(51) Int. Cl.
*A61K 9/14* (2006.01)
*A61M 1/00* (2006.01)

(52) U.S. Cl. .............................. 424/489; 604/27; 604/28

(58) Field of Classification Search ........................ None
See application file for complete search history.

(56) References Cited

U.S. PATENT DOCUMENTS

| | | | |
|---|---|---|---|
| 4,794,931 A | 1/1989 | Yock | |
| 5,000,185 A | 3/1991 | Yock | |
| 5,024,234 A | 6/1991 | Leary et al. | |
| 5,049,130 A | 9/1991 | Powell | |
| 5,100,185 A | 3/1992 | Menke et al. | |
| 5,171,217 A | 12/1992 | March et al. | |
| 5,202,745 A | 4/1993 | Sorin et al. | |
| 5,203,338 A | 4/1993 | Jang | |
| 5,291,267 A | 3/1994 | Sorin et al. | |
| 5,321,501 A | 6/1994 | Swanson et al. | |
| 5,365,325 A | 11/1994 | Kumasaka et al. | |
| 5,372,138 A | 12/1994 | Crowley et al. | |
| 5,459,570 A | 10/1995 | Swanson et al. | |
| 5,464,395 A | 11/1995 | Faxon et al. | |
| 5,465,147 A | 11/1995 | Swanson | |
| 5,485,486 A | 1/1996 | Gilhousen et al. | |

(Continued)

FOREIGN PATENT DOCUMENTS

GB 2194144 3/1988

(Continued)

OTHER PUBLICATIONS

"Vessel". Stedman's Medical Dictionary 27th Edition. Accessed online on Nov. 7, 2007 at http://www.thomsonhc.com.*

(Continued)

*Primary Examiner*—Humera N Sheikh
(74) *Attorney, Agent, or Firm*—Blakely Sokoloff Taylor & Zafman LLP (57) ABSTRACT

A method including positioning a delivery device at a location in a vessel within a mammalian body, introducing a first treatment agent including a cellular component through the delivery device, and introducing a different second treatment agent disposed in a carrier through the delivery device. A method including identifying an infarct region within myocardial tissue and a border region of perfused tissue adjacent the infarct region, introducing a treatment agent including a cellular component to the border region, and introducing a plurality of microparticles to the infarct region. A kit including a treatment agent including a cellular component in a form suitable for percutaneous delivery, and a separate amount of a plurality of microparticles in a form suitable for percutaneous delivery.

12 Claims, 6 Drawing Sheets

U.S. PATENT DOCUMENTS

| | | | |
|---|---|---|---|
| 5,499,630 | A | 3/1996 | Hiki et al. |
| 5,546,948 | A | 8/1996 | Hamm et al. |
| 5,580,856 | A | 12/1996 | Prestrelski et al. |
| 5,588,432 | A | 12/1996 | Crowley |
| 5,693,029 | A | 12/1997 | Leonhardt |
| 5,722,403 | A | 3/1998 | McGee et al. |
| 5,740,808 | A | 4/1998 | Panescu et al. |
| 5,827,313 | A | 10/1998 | Ream et al. |
| 5,843,156 | A | 12/1998 | Slepian et al. |
| 5,874,500 | A | 2/1999 | Rhee et al. |
| 5,879,713 | A | 3/1999 | Roth et al. |
| 5,900,433 | A | 5/1999 | Igo et al. |
| 5,941,868 | A | 8/1999 | Kaplan et al. |
| 5,957,941 | A | 9/1999 | Ream |
| 5,968,064 | A | 10/1999 | Selmon |
| 5,981,568 | A | 11/1999 | Kunz et al. |
| 6,045,565 | A | 4/2000 | Ellis et al. |
| 6,051,648 | A | 4/2000 | Rhee et al. |
| 6,056,744 | A | 5/2000 | Edwards |
| 6,099,864 | A | 8/2000 | Morrison et al. |
| 6,102,904 | A | 8/2000 | Vigil et al. |
| 6,120,520 | A | 9/2000 | Saadat et al. |
| 6,133,231 | A | 10/2000 | Ferrara et al. |
| 6,134,003 | A | 10/2000 | Tearney et al. |
| 6,159,443 | A | 12/2000 | Hallahan et al. |
| 6,175,669 | B1 | 1/2001 | Colston et al. |
| 6,177,407 | B1 | 1/2001 | Rodgers et al. |
| 6,179,809 | B1 | 1/2001 | Khairkhahan et al. |
| 6,183,432 | B1 | 2/2001 | Milo |
| 6,187,330 | B1 | 2/2001 | Wang et al. |
| 6,190,353 | B1 | 2/2001 | Makower et al. |
| 6,191,144 | B1 | 2/2001 | Isner |
| 6,193,763 | B1 | 2/2001 | Mackin |
| 6,197,324 | B1 | 3/2001 | Crittenden |
| 6,201,608 | B1 | 3/2001 | Mandella et al. |
| 6,207,180 | B1 | 3/2001 | Ottoboni et al. |
| 6,210,392 | B1 | 4/2001 | Vigil et al. |
| 6,217,527 | B1 | 4/2001 | Selmon et al. |
| 6,217,554 | B1 | 4/2001 | Green |
| 6,221,049 | B1 | 4/2001 | Selmon et al. |
| 6,231,546 | B1 | 5/2001 | Milo et al. |
| 6,235,000 | B1 | 5/2001 | Milo et al. |
| 6,290,729 | B1 | 9/2001 | Slepian et al. |
| 6,296,602 | B1 | 10/2001 | Headley |
| 6,312,725 | B1 | 11/2001 | Wallace et al. |
| 6,323,278 | B2 | 11/2001 | Rhee et al. |
| 6,328,229 | B1 | 12/2001 | Duronio et al. |
| 6,494,862 | B1 | 12/2002 | Ray et al. |
| 6,554,801 | B1 | 4/2003 | Steward et al. |
| 6,624,245 | B2 | 9/2003 | Wallace et al. |
| 6,692,466 | B1 | 2/2004 | Chow et al. |
| 2003/0040712 | A1 | 2/2003 | Ray et al. |
| 2004/0181206 | A1 | 9/2004 | Chiu et al. |
| 2005/0015048 | A1 | 1/2005 | Chiu et al. |
| 2005/0070844 | A1 | 3/2005 | Chow et al. |
| 2005/0281883 | A1 | 12/2005 | Daniloff et al. |

FOREIGN PATENT DOCUMENTS

| | | |
|---|---|---|
| WO | WO-0124775 | 4/2001 |
| WO | WO 0149357 | 7/2001 |
| WO | WO 02/40070 | 5/2002 |
| WO | WO 02/087623 | 11/2002 |
| WO | 03/064637 A1 * | 8/2003 |
| WO | WO 03/064637 | 8/2003 |
| WO | WO 03064637 A1 * | 8/2003 |
| WO | WO 2004/050013 | 6/2004 |
| WO | WO 2004/091592 | 10/2004 |

OTHER PUBLICATIONS

PCT/US2005/045627, filed Dec. 16, 2005, "International Search Report and Written Opinion of the International Search Authority," dated Oct. 13, 2006.

Kawai, K, et al., "Accelerated tissue regeneration through incorporation of basic fibroblast growth factor-impregnated gelatin microspheres into artificial dermis," Biomaterials, Mar. 2000, 21(5):489-99.

Rowley, JA, et al., "Alginate hydrogels as synthetic extracellular matrix materials," Biomaterials, Jan. 1999, 20(1):45-53.

Haugland, RP, "Membrane-Permeant Reactive Tracers," In: Gregory J, ed. Handbook of Fluorescent Probes and Research Products. Eugene: Molecular Probes, Inc., 2002:458-553.

Haugland, RP, "Dialkylcarbocyanine and Dialkylaminostyryl Probes," In: Gregory J, ed. Handbook of Fluorescent Probes and Research Products. Eugene: Molecular Probes, Inc., 2002:530-534.

Nose, A, et al., "A Novel Cadherin Cell Adhesion Molecule: Its Expression Patterns Associated with Implantation and Organogenesis of Mouse Embryos," Journal of Cell Biology, vol. 103 (No. 6, Pt. 2), Dec. 1986, 2649-2658.

Chandy, et al., "The development of porous alginate/elastin/PEG composite matrix for cardiovascular engineering", Journal of Biomaterials Applications, vol. 17, Apr. 2003, pp. 287-301.

Dinbergs, et al., "Cellular response to transforming growth factor-β1 and basic fibroblast growth factor depends on release kinetics and extracellular matrix interactions", The Journal of Biological Chemistry, vol. 271, No. 47, Nov. 1996, pp. 29822-29829.

Edelman, et al., "Controlled and modulated release of basic fibroblast growth factor", Biomaterials, vol. 12, Sep. 1999, pp. 619-626.

Johnson, et al., "The stabilization and encapsulation of human growth hormone nto biodegradable microspheres", Pharmaceutical Research, vol. 14, No. 6, 1997, pp. 730-735.

Shin, et al., "In vivo bone and soft tissue response to injectable, biodegradable oligo(poly(ethylene glycol) fumarate) hydrogels", Biomaterials 24, Elseview Science Ltd., 2003, pp. 3201-3211.

* cited by examiner

TISSUE REGENERATION

BACKGROUND

1. Field

Inducing formation of blood vessels through therapeutic angiogenesis and/or therapeutic angiomyogenesis.

2. Relevant Art

A major component of morbidity and mortality attributable to cardiovascular disease occurs as a consequence of the partial or complete blockage of vessels carrying blood in the coronary and/or peripheral vasculature. When such vessels are partially occluded, lack of blood flow causes ischemia to the muscle tissues supplied by such vessel, consequently inhibiting muscle contraction and proper function. Total occlusion of blood flow causes necrosis of the muscle tissue.

Blood vessel occlusions are commonly treated by mechanically enhancing blood flow in the affected vessels. Such mechanical enhancements are often provided by employing surgical techniques that attach natural or synthetic conduits proximal and distal to the areas of occlusion, thereby providing bypass grafts, or revascularization by various means to physically enlarge the vascular lumen at the site of occlusion. These revascularization procedures involve such devices as balloons, endovascular knives (atherectomy), and endovascular drills. The surgical approach is accompanied by significant morbidity and even mortality, while the angioplasty-type processes are complicated by recurrent stenoses in many cases.

In some individuals, blood vessel occlusion is partially compensated by natural processes, in which new vessels are formed (termed "angiogenesis") and small vessels are enlarged (termed "arteriogenesis") to replace the function of the impaired vessels. These new conduits may facilitate restoration of blood flow to the deprived tissue, thereby constituting "natural bypasses" around the occluded vessels. However, some individuals are unable to generate sufficient collateral vessels to adequately compensate for the diminished blood flow caused by cardiovascular disease. Accordingly, it would be desirable to provide a method and apparatus for delivering agents to help stimulate the natural process of therapeutic angiogenesis to compensate for blood loss due to an occlusion in coronary and peripheral arteries in order to treat ischemia.

Myocardial infarction (MI) is one form of a cardiac event that causes the sudden lack of supply of oxygen and other nutrients to the myocardium. The lack of blood supply is a result of closure of the coronary artery that nourishes a particular part of the heart muscle. The cause of this event is generally caused by arteriosclerosis "hardening of the arteries" in coronary vessels, or as a result of the formation of thrombi by the rupture of unstable plaque.

Even though relatively effective systemic drugs exist to treat MI such as ACE-inhibitors and Beta-blockers, a significant portion of the population that experiences a major MI ultimately develop heart failure. An important component in the progression to heart failure is remodeling of the heart due to mechanical forces resulting in uneven stress and strain distribution in the left ventricle. Once an MI occurs remodeling of the heart begins. The principal components of the remodeling event include myocyte death, edema and inflammation, followed by fibroblast infiltration and collagen deposition, and finally scar formation. The principal component of the scar is collagen. Since mature myocytes of an adult are not regenerated the infarct region experiences significant thinning. Myocyte loss is the major etiologic factor of wall thinning and chamber dialation that may ultimately lead to progression of cardiac myopathy. In other areas, remote regions experience hypertrophy (thickening) resulting in an overall enlargement of the left ventricle. This is the end result of the remodeling cascade. These changes in the heart result in changes in the patient's lifestyle and their ability to walk and to exercise. These changes also correlate with physiological changes that result in increase in blood pressure and worsening systolic and diastolic performance.

Accordingly, it would be desirable to provide a method and apparatus for delivery agents that stabilize a ventricle (e.g., the left ventricle) and/or stimulate cell growth (e.g., muscle cell growth).

SUMMARY

A method is disclosed. In one embodiment, a method includes positioning a delivery device at a location in a vessel within a mammalian body. The method also includes introducing a first treatment agent including a cellular component through the delivery device and introducing a different second treatment agent disposed in a carrier through the delivery device. The first treatment agent and the second treatment agent may be introduced contemporaneously (concommittantly). In one example, each of the first treatment agent and the second treatment agent may be delivered to myocardium to affect an infarct region. Representatively, the first treatment agent may be introduced to a perfused region of myocardium adjacent an infarct region, such as a border zone around an infarct region. The second treatment agent may be introduced into the infarct region.

In one embodiment, an infarct region may be affected in an effort to regenerate tissue or replace/introduce myocytes in the infarct region. Representatively, a second treatment agent including a factor that affects therapeutic angiogenesis or angiomyogenesis may be introduced to the infarct region. Alternatively or additionally, the second treatment agent may include an attractant or homing factor that has a property that tends to draw or attract cellular components. Accordingly, introducing a first treatment agent in perfused tissue will increase the viability of the cellular component and the presence of a second treatment agent including a homing factor will draw the cellular component into the infarct region to regenerate tissue within that region. In one embodiment, the carrier associated with the second treatment includes a plurality of microparticles (e.g., microspheres) that collectively provide a release rate gradient of the second treatment agent.

A kit is also disclosed. In one embodiment, the kit includes a first treatment agent comprising a cellular component in a form suitable for percutaneous delivery and a separate amount of a second treatment agent disposed a plurality of microparticles also in a form suitable for percutaneous delivery. A portion of the plurality of microparticles may include a factor that affects therapeutic angiogenesis, angiomyogenesis, an attractant or homing factor. The plurality of microparticles may have a property that when taken collectively provide a release rate gradiant of factors associated with the microparticles. Each of the first treatment agent and the plurality of microparticles are present in the kit, for example, at a targeted dose to induce or modulate therapeutic angiomyogenesis or therapeutic angiogenesis.

The features of the described embodiments are specifically set forth in the appended claims. However, the embodiments are best understood by referring to the following description and accompanying drawings, in which similar parts are identified by like reference numerals.

DETAILED DESCRIPTION

In connection with the description of the various embodiments, the following definitions are utilized:

"Angiogenesis" is the formation of small blood vessels and capillaries within ischemic tissue.

"Arteriogenesis" is enlargement of existing collateral vessels that typically stem from perfused tissue into ischemic tissue.

"Therapeutic angiogenesis" refers to the processes of causing or inducing angiogenesis and arteriogenesis.

"Myogenesis" is the formation of new myocytes.

"Angiomyogenesis" is the combination of angiogenesis and myogenesis, where myocardial tissue including new blood vessels as well as muscle components is formed.

"Therapeutic angiomyogenesis" refers to the process of causing or inducing angiomyogenesis.

"Carrier" includes a matrix that contains one or more treatment agents. A suitable carrier may take the form of a nanoparticle (e.g., nanosphere), microparticle (e.g., microsphere) or gel with a therapeutic agent as the situation may dictate.

Figure 1:
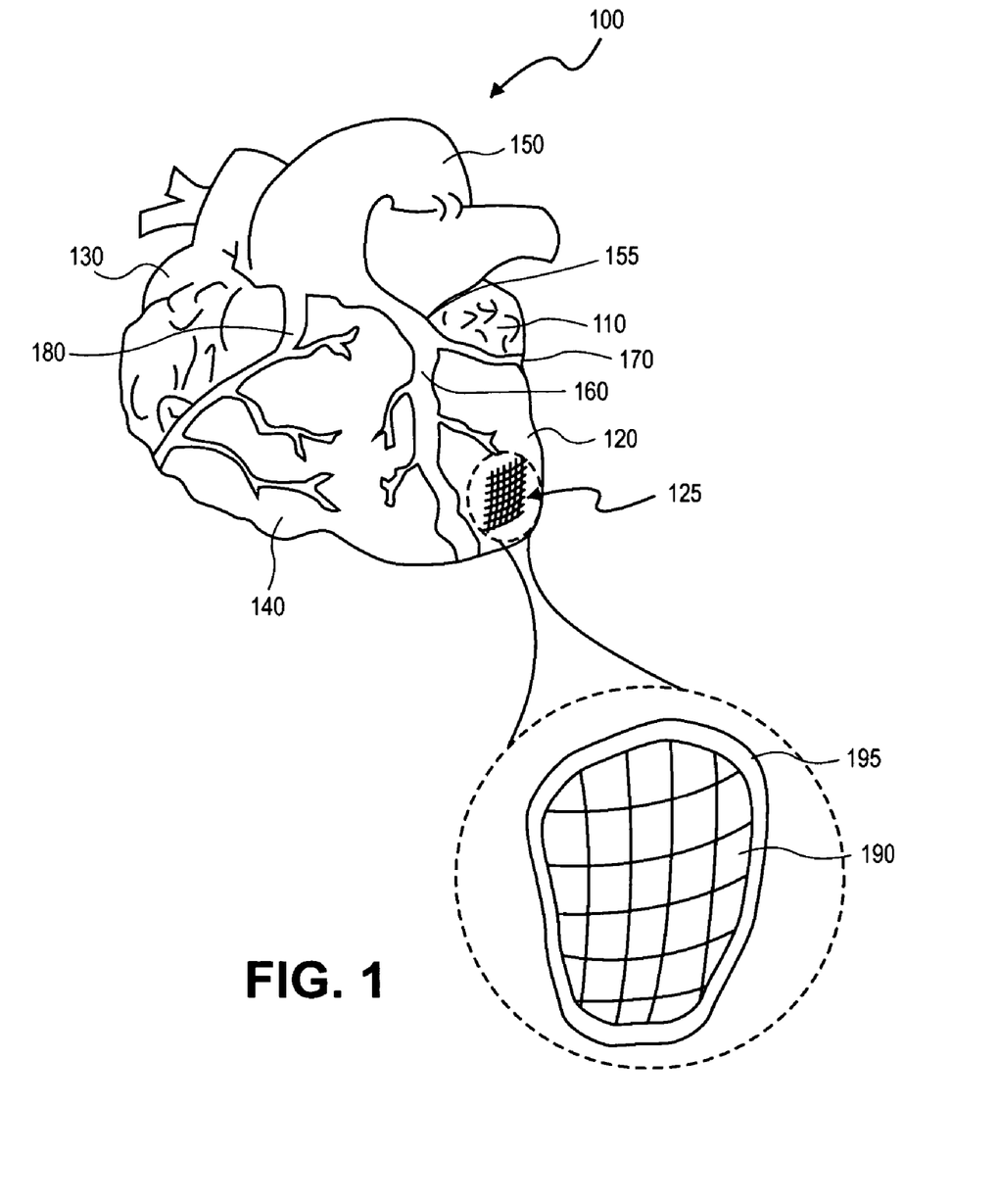
FIG. 1 shows an anterior perspective view of a heart having an infarct region associated with the left ventricle.

FIG. 1 shows a schematic view of a portion of a human heart. Representatively, heart 100 includes left atrium 110, left ventricle 120, right atrium 130, and right ventricle 140. In this illustration, various arteries are shown. Included in FIG. 1 are aorta 150, left anterior descending artery (LAD) 160, left circumflex artery (LCX) 170 and right coronary artery (RCA) 180. Site 125, in this embodiment, has been damaged by an MI due to, for example, a lack of blood supply due to a partial closure or closure of LAD 160 or LCX 170 or both. The damage is representatively illustrated at the base of left ventricle 120. Representatively, the damage includes thinning of the muscle tissue of left ventricle 120.

FIG. 1 also shows a magnified view of site 125. In this view, site 125 includes necrotic or infarct region 190. Necrotic or infarct region 190 may or may not include viable myocytes and consists primarily of fibroblasts and/or collagen depending on how recent the MI event occurred. For instance, if the MI event occur within a few weeks of identification, then there may be viable myocytes remaining in infarct region 190 along with fibroblasts and some collagen formation. Longer periods of time between an MI event and identification would tend to reveal few, if any, viable myocytes in infarct region 190 and predominantly collagen.

The magnified view of site 125 in FIG. 1 also shows border zone 195 surrounding infarct region 190. In simple terms, an infarcted region, such as infarct region 190, may be thought of as a region devoid of blood supply, resulting in apoptosis and necrosis and accompanying inflammatory response and scar formation. A border zone, such as border zone 195, may have limited blood supply, whereby cells are rendered hypoxic and not fully contractile yet still viable. Cells in the border zone typically will undergo hypertrophy in response to stresses imparted by the thinning of the infarct zone.

To improve the function of left ventricle 120, therapeutic angiomyogenesis may be induced at or near site 125. In one embodiment, therapeutic angiomyogenesis is induced by the introduction of a treatment agent comprising a cellular component (a "first treatment agent") and the concomitant (e.g., contemporaneous) introduction of a different treatment agent (a "second treatment agent") disposed in a carrier. Representatively, acceptable modes of delivery of the first treatment agent and the second treatment agent, include, but are not limited to, vascular infusion and myocardial injection.

First Treatment Agent

In one embodiment, a cellular component for use as part of the first treatment agent includes adult or embryonically-derived stem cells. For example, adult-derived bone marrow cells delivered to ischemic tissue can induce an angiogenic response. Other adult stem cells including, but not limited to, mesenchymal stem cells (MSC), multipotent adult progenator cells (MAPC), and endothelial progenator cells (EPC) may be suitable to induce angiomyogenesis. In another embodiment, suitable cells of a cellular component of the first treatment agent may be transfected with appropriate gene vectors to become more angiogenic or angiomyogenic and/or to improve the cell survival or preservation in the target medium (e.g., an anti-apoptosis and/or an anti-necrosis factor). Examples of suitable survival vectors include HIF1alpha, HIF2alpha, TNF, IL1, and PR39 (angiogenesis/anti-apoptosis). Homing vectors such as SDF-1, IGF, and HGF may also be transfected in another embodiment.

Cellular components, such as the cells noted above, typically have receptors for particular peptide sequences (e.g., cell adhesion ligands) that allow the cellular component to adhere to collagen or other tissue that have receptors. A specific peptide receptor or binding sequence is an arginine-glycine-aspartic acid (RGD) polypeptide. Such receptor allows the cellular components to be delivered in, for example, cardial tissue and be retained to induce or promote angiogenesis and/or angiomyogenesis for collateral formation in the heart as well as in peripheral circulation, such as applications involving stroke, peripheral arterial disease (PAD), etc.

In one embodiment, the first treatment agent may be delivered percutaneously, such as through catheter/needle delivery. Suitable delivery mechanisms include delivery of a treatment agent including an isotonic saline solution of cells, such as stem cells.

Second Treatment Agent

In one embodiment, in addition to introducing a treatment agent including a cellular component (a "first treatment agent"), a method includes introducing a different second treatment agent disposed in a carrier such as a microparticle (e.g., microsphere) or nanoparticle. The second treatment agent may have a property that affects therapeutic angiogenesis or angiomyogenesis. Suitable agents include, but are not limited to, growth factors such as vascular endothelial growth factor (VEGF), basic fibroblast growth factor (bFGF), MCP1, insulin like growth factor 1 (IGF1), HIF1-alpha, PR39 and its derivatives, and agents that induce a mild inflammatory effect such a nicotine or microspheres derived from poly(methacrylic acid-co-methyl methacrylate). In another embodiment, the second treatment agent may have a property that will attract cells (e.g., homing factors). Suitable homing factors include, but are not limited to SDF-1, IGF and HGF.

In one embodiment, a second treatment agent disposed in a carrier may have a property that is auxiliary to affecting therapeutic angiogenesis or therapeutic angiomyogenesis. A treatment agent is auxiliary in the sense that it supplements, assists, or supports the first treatment agent. Representatively, the second treatment agent may have an attractant (e.g., a chemoattractant) property that induces movement of the first treatment agent in its direction. Suitable attractant agents include homing factors such as insulin derived growth factor (IDGF) that encourage cellular components from, for example, the first treatment agent to migrate toward the second treatment agent.

The second treatment agent is disposed in a carrier of a particle, e.g., microparticle or nanoparticle. Representatively, suitable microparticles (e.g., microspheres) have a diameter less then 80 microns, preferably less then 30 microns. According to one embodiment, the release rate of the particle (release rate of the second treatment agent) may vary so that a plurality of particles, intended for percutaneous introduction at a desired or targeted dose, provides a release rate gradient. An example of forming a release rate gradient is to form particles of a carrier that tend to breakdown through degradation or erosion at a different time after introduction at a treatment site. One way to provide a release rate gradient is to introduce the second treatment agent in particles of different sizes, with small sizes (e.g., 5 μm) tending to degrade faster than larger sizes (e.g., 30 μm). A suitable release rate gradient is the release of the second treatment agent from the carrier (particle) over a period of hours to a period of days or weeks (e.g., two weeks). In another embodiment, the release radiant gradient is a release of the second treatment agent over a period of two to three days.

One way to form a second treatment agent disposed in a carrier is to form a carrier particle of a hydrogel, such as alginate-derived hydrogel. Alginates are composed of (1-4)-linked β-D-mannuronic acid (M units) and α-L-guluronic acid (G units) monomers which vary along a polymer chain depending on the source of the alginate. The alginate molecule of a block copolymer is composed of regions of sequential M units, regions of sequential G units, and regions of atactically organized M and G units. Divalent cations like calcium ($Ca^{2+}$) cooperatively bind between the G units of adjacent alginate chains, creating ionic interchain bridges that cause gelling of aqueous alginate solutions.

In one embodiment of forming an alginate hydrogel including an angiogenic/angiomyogenic factor and/or an auxiliary factor, the angiogenic and/or auxiliary factor may be added to a solution of sodium alginate and isotonic saline with optional additional ions (e.g., magnesium, potassium) prior to injection. The alginate may be covalently modified with a cell adhesion ligand such as RGDx, GRTY (where Y is tyrosine), etc., containing peptides via a carbodiimide coupling to improve or enhance cell attachment to the alginate. Attached peptide sequences (e.g., RGDx) provide adhesion of the alginate alginate to cellular receptors or other tissue at the treatment site. A suitable covalent modification with a peptide sequence is described in "*Alginate Hydrogels as Synthetic Extracellular Matrix Materials,*" Rowley, et al., Biomaterials 20 (1999), 45-53. In another embodiment, the alginate may be covalently modified with (e.g., covalently conjugated to) a gelatin or collagen (e.g., a gelatin or collagen commercially available from FibroGen, Inc. of South San Francisco, Calif.).

One way to form particles including an alginate or a modified alginate carrier is by adding an aqueous alginate solution including the angiogenic and/or auxiliary factor to a non-aqueous solvent such as a polyhydric alcohol or methylene chloride and then adding an emulsifying agent to the formed mixture so as to cause an emulsion dispersion (e.g., a water-and-oil type emulsion). The emulsion dispersion may be added to an aqueous solution of a salt such as calcium chloride ($CaCl_2$) to form generally spherical microparticles of an alginate.

Another technique for forming a treatment agent disposed in a carrier in the form of discrete particles (e.g., microspheres) of an alginate hydrogel is to add an angiogenic/angiomyogenic and/or auxiliary factor to a solution of sodium alginate or modified sodium alginate as described above. The solution is placed into a spray gun or an atomizer such as commercially available from Efd-inc of East Providence, R.I. A solution of alginate-covered cells may be sprayed into an agitated solution of calcium chloride ($CaCl_2$). The atomized alginate-covered cells form discrete particles (e.g., microspheres) on exiting the atomizer. When these particles enter the calcium solution, the alginate portion is gelled and becomes generally insoluble in water. The particles may then be separated by centrifugation or filtration, washed, and resuspended in aphysiologically compatible solution such as HYPOTHERMOSOL™, commercially available from BioLife Solutions, Inc. of Binghamton, N.Y. The particles can then be introduced percutaneously either through infusion or injection techniques.

In another embodiment, a treatment agent such as angiogenic and/or auxiliary factor may be disposed in a carrier of a gelatin or collagen. One suitable collagen is commercially available from FibroGen, Inc. of South San Francisco, Calif. Preferably, the immunogenic property of the collagen is minimal.

Comb-like polymers based on alginate-collagen copolymers can also be utilized for the encapsulation of therapeutic agents. The alginate-collagen microspheres are formulated in the manner as described for alginate. In this composition, the collagen possesses endogenous RGDx binding domains.

Representatively, porous gelatin microspheres may be formed such as described in "*Accelerated Tissue Generation Through Incorporation of Basic fibroblastic growth Factor-Impregnated Gelatin Microspheres into Artificial Dermis,*" Kawai et al., Biomaterials 21, (2000), 489-499. The porous gelatin microspheres described in Kawai may be modified by using a water soluble porogen (e.g., polyethylene glycol, sugar, etc.) in the initial water in oil emulsion. The spheres are allowed to cross-link with glutaraldehyde or genepin, then the porogen can be dissolved by soaking in water to yield porous particles (e.g., microspheres). The porous particles may be seeded with a treatment agent including angiogenic/angiomyogenic and/or auxiliary factors by dropping an aqueous solution of the treatment agent into the particles. The factors will tend to attach to the particles.

A still further example of a second treatment agent disposed in a carrier is the use of encapsulation polymers as carriers such as poly (L-lactide), poly (D,L-lactide), poly (glycolide), poly (lactide-co-glycolide), polycaprolactone, polyanhydride, polydiaxanone, polyorthoester, polyamino acids, or poly (trimethylene cabonate), and combinations thereof. One example of a carrier composition that can be used to form particles providing a release rate gradient response is a poly (DL-lactide-co-glycolide) (PLGA) system. With this system, the rate of breakdown of the treatment agent can be controlled through a selection of the copolymer ratio, the molecular weight of the polymer, thermal and post-processing history (or intrusion, etc.) and the presence of acid end group. A 50:50 copolymer ratio is usually considered to be rapidly degrading, while increased copolymer ratios in either direction result in reduced degradation rates because of a balance between increased hydrophobicity with higher poly (lactic acid) PLA) content and increased crystallinity with higher poly (glycolic acid) (PGA) content. The rate of degradation can be increased with acid end groups and by reducing the molecular weight of the polymer.

Polyanhydrides may also be formed as carriers. In terms of polyanhydrides, degradation rates can be modified to provide a release rate gradient by utilizing copolymers of methacrylated bis (p-carboxyphenoxy) hexane (MCPH) and methacrylated sebacic acid (MSA). Polyhydroxyalkanoates (PHA) such as polyhydroxybutyrate (PHB) or polyhydroxyvalerate (PHV) or a copolymer thereof is another example for controlling degradation rates of polyanhydrides. The degradation profile may be also be influenced by a blended system to induce multi-modal degradation profiles (e.g., slow degradation during first week, fast degradation during second week, etc.).

Polymer-based carriers (e.g., gel-like bodies) may be formed before introduction at a treatment site (in vitro) or they may be formed in vivo. One way to form such microspheres in vivo is by desolving a blend of, for example, fast and slow degrading polymers in water misable solvents such as dimethyl sulfoxide (DMSO), N-methylpyrrolidone (NMP), ethanol or glycofural and injecting the solution at the site of treatment with, for example, a catheter to precipitate out polymer particles. Several polymer solutions, each consisting of a polymer formulation with a different degradation rate can alternatively be introduced in sequence to precipitate out a mixed population of polymer microparticles.

Methods of Delivery

In one embodiment, the treatment agent including a cellular component (first treatment agent) is introduced to improve oxygen perfusion within the myocardium, such as border zone 195 of site 125 in FIG. 1. Perfuse myocardium, including border zone 195, tends to encourage cellular proliferation and differentiation. Because the first treatment agent is delivered to improve the perfusion of myocardium, the viability of the cellular component of the first treatment agent will be enhanced. At approximately the same time, the border zone and/or an infarct region, such as infarct region 190 in FIG. 1 is seeded with the second treatment agent disposed in a carrier. Representatively, microparticles or nanoparticles (microspheres) including the second treatment agent are seeded in the border zone and/or infarct region. The selected delivery of the first treatment agent to perfuse regions and the second treatment agent to infarct regions may enhance migration of cellular components into the infarct region (particularly if the second treatment agent includes an attractant) and enhance perfusion of the infarct region. In this manner, an infarct region can be reperfused and the extracellular matrix modified to support cellular migration.

As noted above, in one embodiment, the first treatment agent and the second treatment agent may be introduced by vascular infusion or myocardial injection or some combination of vascular infusion and a myocardial injection. Delivery of the first treatment agent by way of myocardial injection technique allows dense seeding of a number of cells, particularly in a location that would contact with a needle mechanism in a targeted location. Delivery of the first treatment agent by way of an infusion method tends to seed cells more sparsely but delivery into an infarcted or scar region may be limited since the number of capillaries that perfuse an infarct region (e.g., site 125 of FIG. 1) through which infusion techniques deliver the treatment agent is low (on the order of 10 percent of healthy tissue or less). Accordingly, cells delivered by a vascular infusion method tend to reside in border zone 195. In one embodiment, it is desired to deliver the second treatment agent to an infarct region. Where the number of capillaries that perfuse an infarct region are limited, such as several weeks after an MI event, the number of capillaries in the infarct region may be low. Therefore, introduction of the second treatment agent into an infarct region by infusion may not be indicated. In such case, the second treatment agent may be introduced by myocardial injection.

Vascular infusion techniques include intra-coronary and coronary sinus retrograde infusion technique. Devices and methods for vascular infusion are described in U.S. patent application Ser. No. 10/387,048, titled *"Retrograde Pressure Regulated Infusion,"* filed Mar. 12, 2003, and U.S. patent application Ser. No. 10/800,323, titled *"Infusion Treatment Agents, Catheters, Filter Devices, and Occlusion Devices, and Use Thereof,"* which are each incorporated herein by reference. Myocardial injection techniques include, but are not limited to, intra-vascular and intra-myocardial techniques. Representative devices and methods for intra-vascular and intra-myocardial injection are described in commonly-known U.S. Pat. No. 6,494,862, titled *"Substance Delivery Apparatus and a Method of Delivering a Therapeutic Substance to an Anatomical Passageway,"* and its related patent documents, and U.S. patent application Ser. No. 09/746,498, titled *"Drug Delivery Catheter with Retractable Needle,"* which are each incorporated herein by reference. Devices and techniques for intra-myocardial injection are described in commonly-owned U.S. patent application Ser. No. 10/676,616, titled *"The Flexible Catheter Assembly and Method of Making Same,"* filed Sep. 30, 2003, which is incorporated herein by reference.

Figure 2:
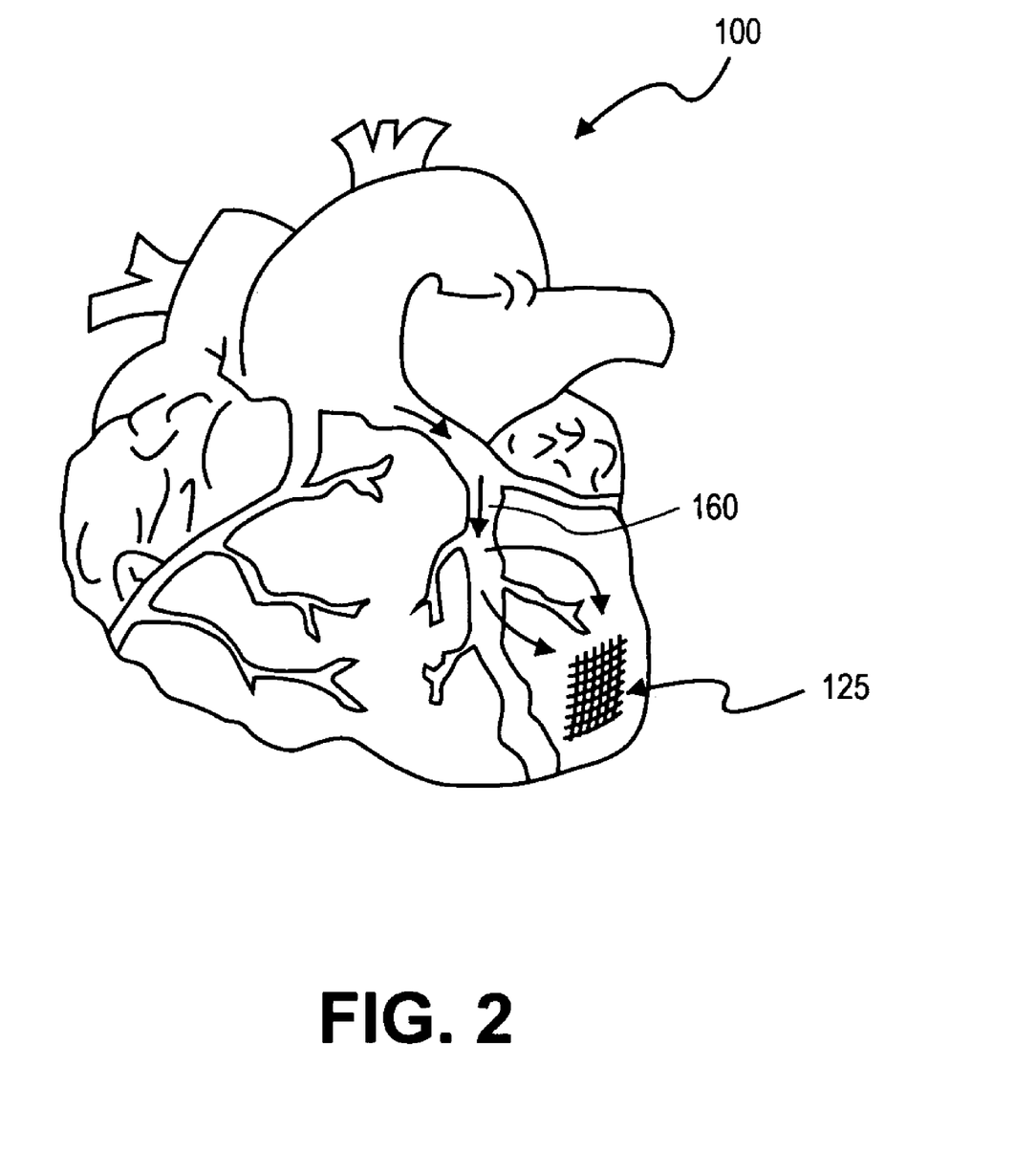
FIG. 2 shows an anterior perspective view of the heart of FIG. 1 and illustrates an intra-coronary vascular infusion procedure to effect the infarct region.

FIG. 2 shows an intra-coronary vascular infusion technique to introduce a first treatment agent and a second treatment agent. In this embodiment, a catheter may be inserted in or adjacent to left anterior descending artery (LAD) 160. Representatively, a catheter may be inserted from a femoral artery and guided using, for example, guidance aids such as fluoroscopy techniques and/or other imaging aids. In one embodiment, a target injection site, such as site 125, is typically identified prior to the delivery procedure. In one embodiment, the first treatment agent and the second treatment agent are concurrently introduced into LAD 160 and introduced at a flow rate and pressure to infuse through a capillary bed at or adjacent to site 125. In one embodiment, second treatment agent disposed in a microparticle (e.g., microsphere) is infused at a perfused region of myocardium including border zone of site 125 (e.g., border zone 195 of FIG. 1) to induce therapeutic arteriogenesis and angiogenesis. Separately, the first treatment agent described above is introduced in LAD 160 and infused into an infarct region at site 125 (infarct region 190 of FIG. 1). The cellular component, for example adult stem cells of the first treatment agent, in this embodiment, may be transfected with appropriate cell preservation and survival gene vectors.

Figure 6:
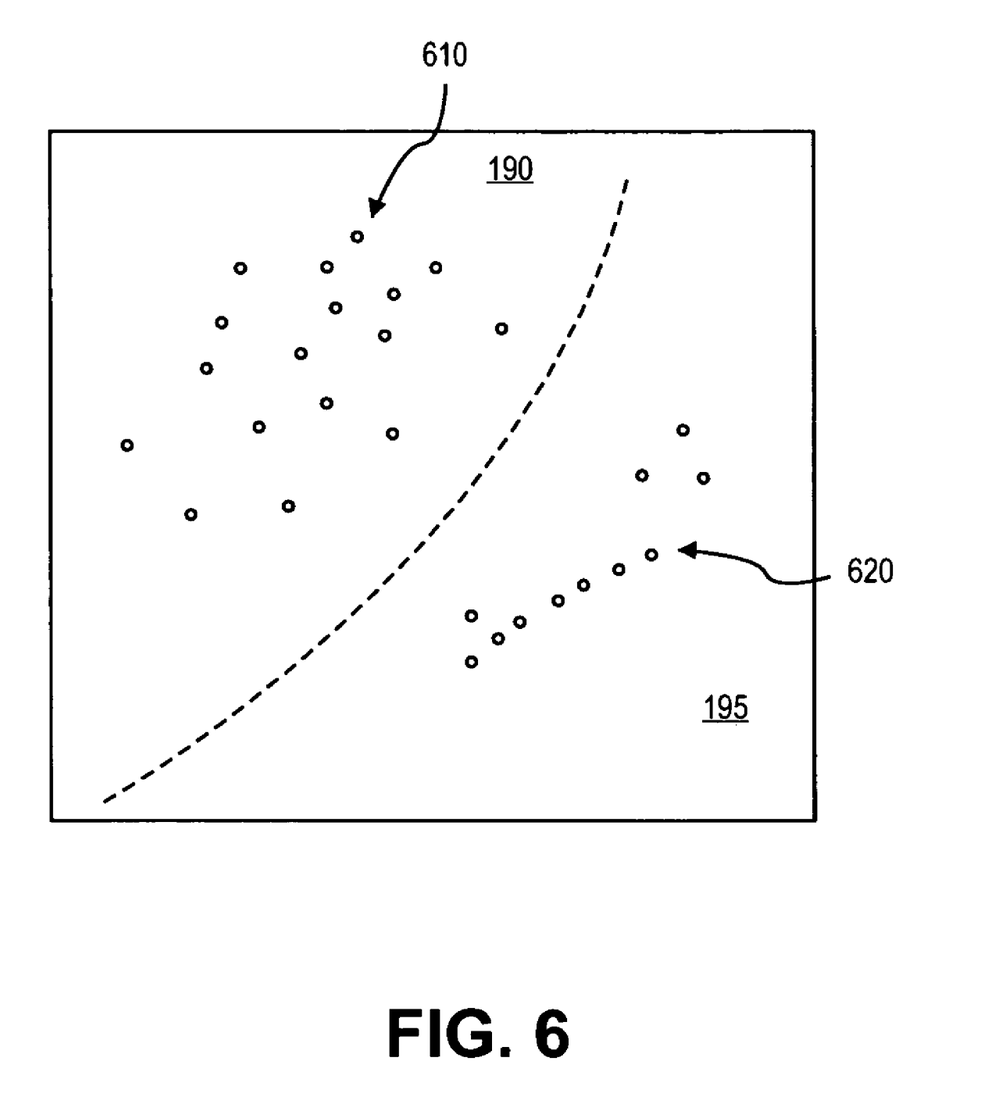
FIG. 6 shows a representation of a histological image of the infracted and borderzone myocardium 7 days after an acute myocardial infarction with stems cells within the infarct and 15 micron microspheres located within the borderzone.

FIG. 6 shows a representation of a histological image of an infarcted and border zone porcine myocardium seven days after an acute myocardial infarction. According to an example performed according to the method described in FIG. 2, FIG. 6 shows bone marrow mononuclear stem cells (BMMSC) 610 infused into infarct region 190 and 7 micron and 15 micron microspheres 620 in border zone 195. As noted above, an infarct region may contain a viable capillary bed(s) at this stage after an infarction, however, the bed(s) may not be accessible by stem cells 610 or microspheres 620 due, for example, to blockage. The representation in FIG. 6 shows stem cells 610 migrate to the infarct region 190 while microspheres reside in border zone 195. To improve the viability of stem cells 610, the cells may be transfected with survival vectors. Alternatively, or additionally, homing vectors or factors may be placed in microspheres 195 to attract cells 610 to border zone 620 which has viable capillary beds. For example, microspheres containing homing vectors may attract cells 610 in infarct region 190 to border zone 195.

Figure 3:
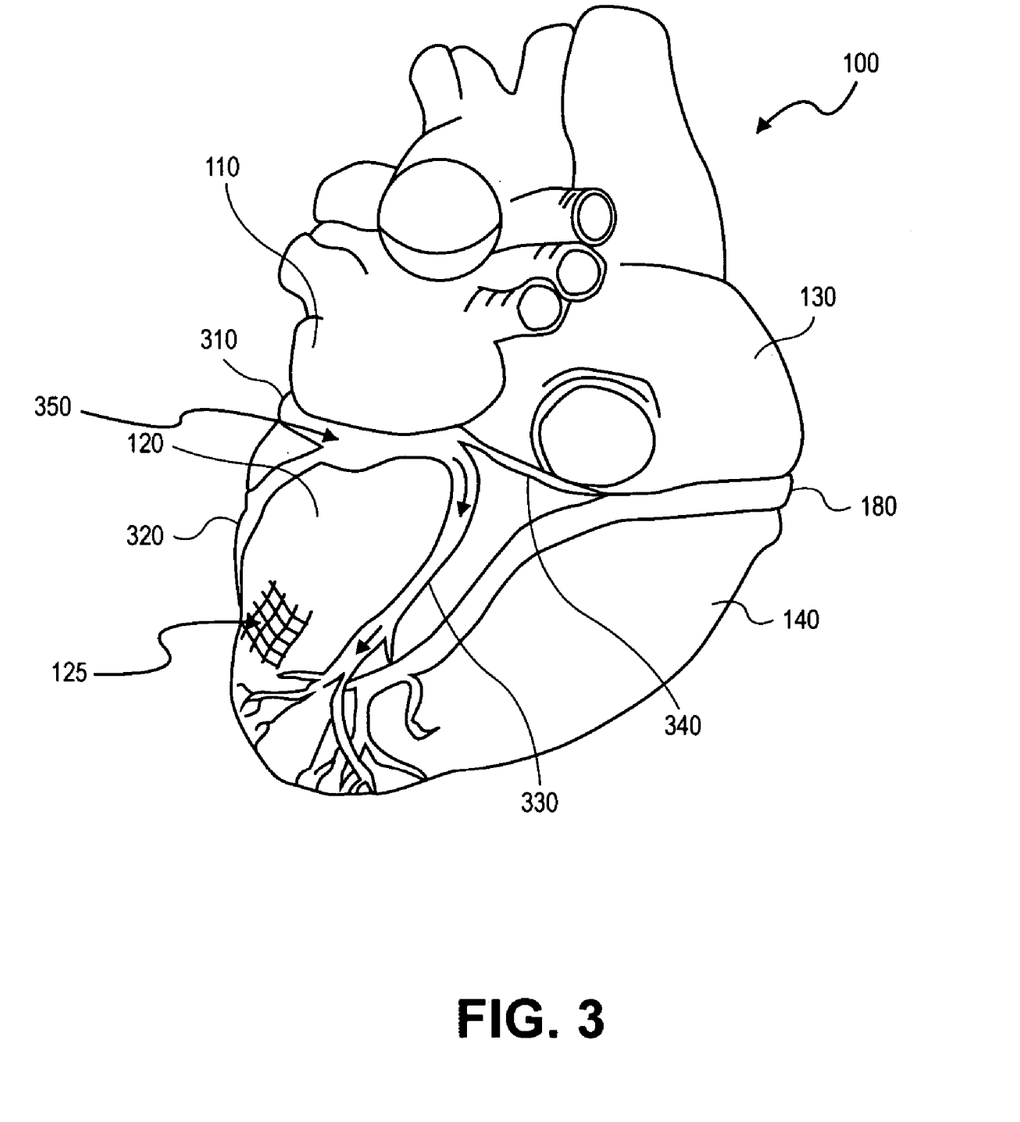
FIG. 3 shows a perspective diaphragmatic view of the heart of FIG. 1 and illustrates a retrograde infusion technique to effect the infarct region.

FIG. 3 shows a coronary sinus retrograde vascular infusion technique to introduce a first treatment agent and a different second treatment agent. FIG. 3 shows a view of the diaphragmatic surface of heart 100. In this view, left atrium 110, left ventricle 120, right atrium 130 and left ventricle 140 are labeled to illustrate the orientation relative to FIG. 1 and FIG. 2. FIG. 3 also shows a portion of the venous system of heart 100. Included in this view are great cardiac vein 310, left posterior ventricular vein 320, middle cardiac vein 330 and small cardiac vein 340.

In one embodiment, a catheter assembly is percutaneously introduced through, for example, a femoral vein to the venous system of heart 100. An occluding balloon may be positioned upstream of one or more veins, such as in great cardiac vein 310 or coronary sinus 350, to occlude blood flow. The catheter assembly may then introduce first treatment agent and a second treatment agent in a retrograde (opposite blood flow (downstream)) fashion. In one embodiment, a pressure and volumetric flow rate of each of the first treatment agent and the second treatment agent are maintained sufficiently high so that the treatment agent will pass in a retrograde direction through middle cardiac vein 330 and reach capillary bed adjacent site 125 of left ventricle 120. In one embodiment, the first treatment agent is introduced into perfused tissue such as the border zone of site 125 (e.g., border zone 195 of FIG. 1). The second treatment agent is separately introduced into an infarct region of site 125 (e.g., infarct region 190 of FIG. 1).

Figure 4:
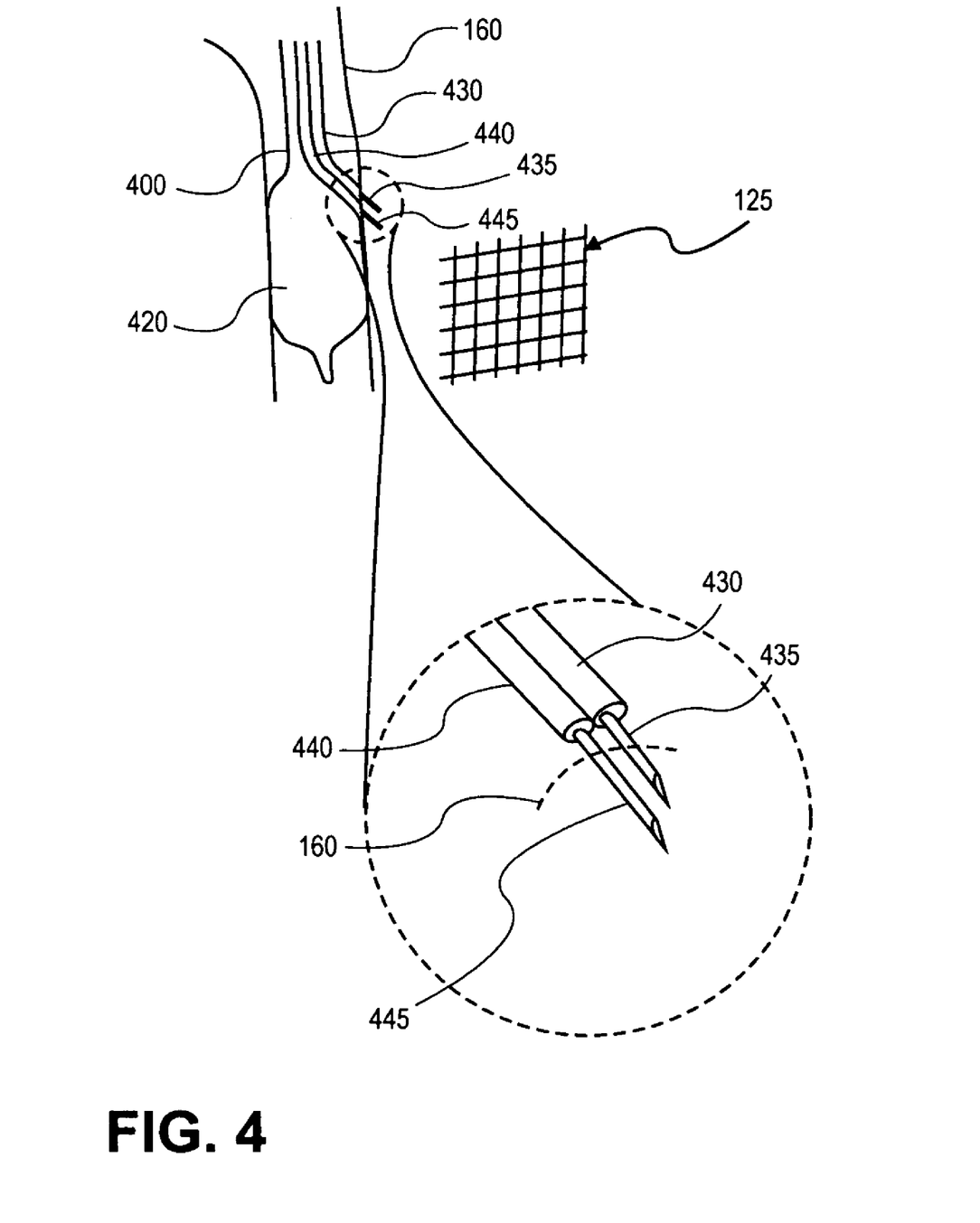
FIG. 4 shows a portion of a left anterior descending artery of the heart of FIG. 1 and a portion of a catheter assembly disposed therein in the illustrating of intra-vascular injection technique to effect the infarct region.

In addition to infusion techniques, in another embodiment, the first treatment agent and/or the second treatment agent may be introduced through myocardial injection. FIG. 4 shows an example of intra-vascular myocardial injection. In this representation, catheter assembly 400 is inserted in LAD 160 and positioned, possibly with guidance techniques, at a location in the vicinity of site 125. Catheter assembly 400 includes balloon catheter 420. Catheter assembly 400 also includes delivery cannula 430 and delivery cannula 440. Each of delivery cannula 430 and delivery cannula 440 may extend from a proximal end of catheter assembly 400, representatively, introduced through a femoral artery. Delivery cannula 430 includes needle 435 and delivery cannula 440 includes needle 445. In this embodiment, delivery-cannula 430 and delivery cannula 440 are located adjacent one another on a proximal portion of balloon 420. In this manner, expansion of balloon 420 within LAD 160 (as shown) causes delivery cannula 430 and delivery cannula 440 to be positioned adjacent the vessel wall of LAD 160. Needle 435 and needle 445 may then be advanced through the vessel wall and beyond the blood vessel wall into or adjacent myocardial tissue. In one embodiment, a first treatment agent including a cellular component is introduced through needle 445 and a second treatment agent disposed in a carrier, such as microparticles (e.g., microspheres) is introduced through needle 445. The first treatment agent is introduced to perfused tissue at or near site 125 (e.g., including at border zone 195 of FIG. 1) while the second treatment agent is introduced into infarcted tissue associated with site 125 (e.g., infarct region 190 of FIG. 1).

Figure 5:
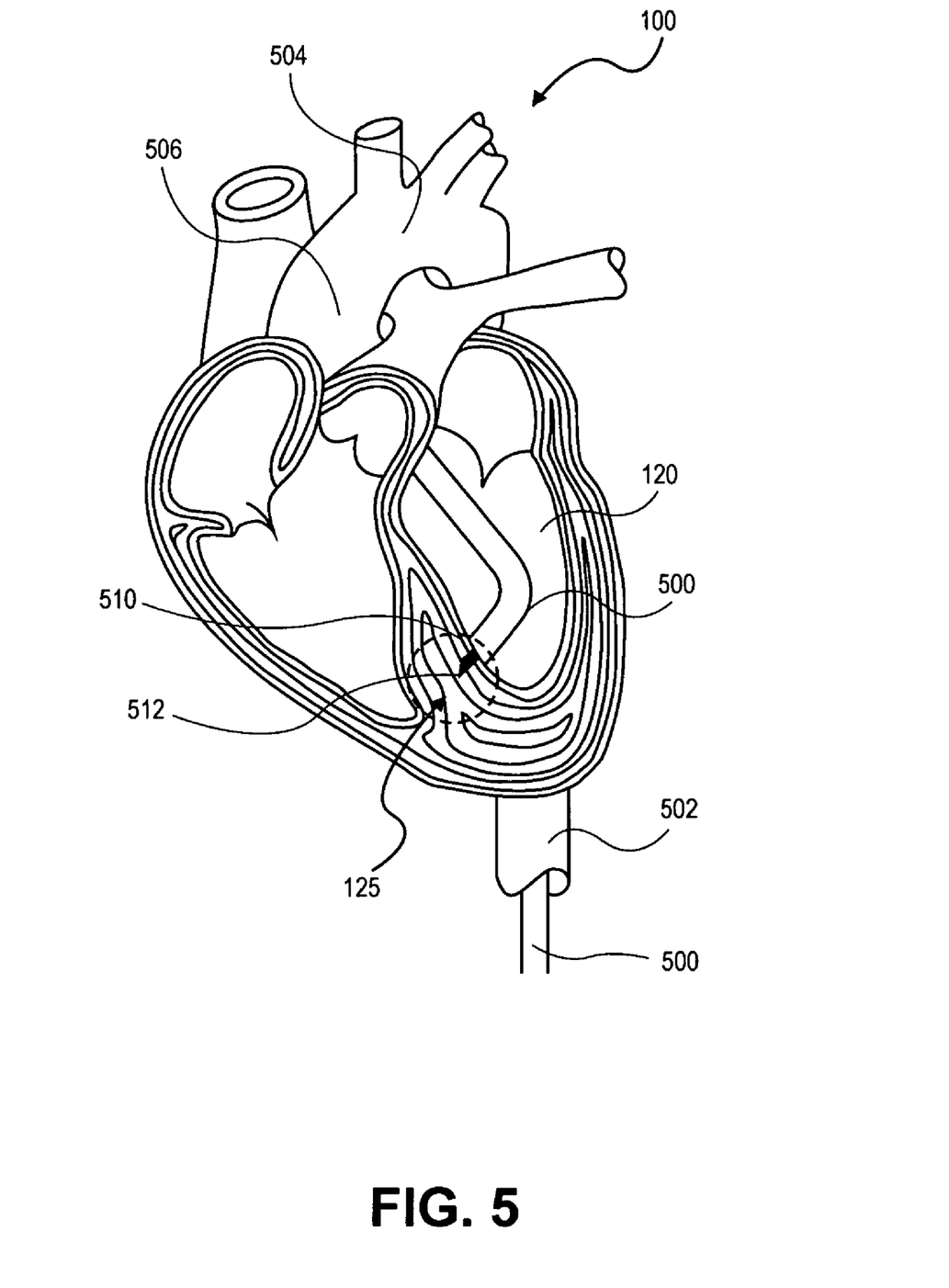
FIG. 5 shows an opened anterior perspective view of the heart of FIG. 1 and demonstrates an intra-myocardial injection technique to effect the infarct region.

A second myocardial injection technique is illustrated in FIG. 5. FIG. 5 shows an interior view of an open heart (heart 100). FIG. 5 shows an embodiment where a catheter assembly is used to delivery a first treatment agent including a cellular component and a second treatment agent disposed in a carrier into the left ventricle of heart 100. A distal portion of catheter assembly 500 is shown disposed in left ventricle 120. Representatively, catheter assembly 500 is inserted into a femoral artery and travels into descending aorta artery 502, over aortic arch 504, down descending aorta 506, across the aortic valve (not shown), and into left ventricle 120. A target injection site such as site 125 has been determined prior to the delivery procedure. Catheter assembly 500 is manipulated to target location 510. Once a tip of catheter assembly 500 is in contact with a wall of left ventricle 120 at a target site, needle 512 is extended into the wall and a treatment agent is released. In one embodiment, a first treatment agent including a cellular component may be introduced through catheter assembly 600 to an area of perfused tissue adjacent site 125 (e.g., including border zone 195 of FIG. 1). Following the introduction of the first treatment agent, a second treatment agent disposed in a carrier such as microparticles (e.g., microspheres) may be introduced through catheter assembly 500 through an infarct region associated with site 125 (infarct region 190 of FIG. 1).

The vascular infusion and myocardial injection techniques described above are representative of modes of delivery for introducing a first treatment agent and a second treatment agent. It is appreciated that the various modes of delivery may be used individually as described or combined with one another to deliver either of the first treatment agent or the second treatment agent. The techniques described above were in reference to affecting myocardial tissue. It is also appreciated that the techniques and kit may be used to affect damaged or distressed tissue in other parts of a body. One example is treating lesions or scars resulting from peripheral artery disease.

In the preceding detailed description, reference is made to specific embodiments thereof. It will, however, be evident that various modifications and changes may be made thereto without departing from the broader spirit and scope of the following claims. The specification and drawings are, accordingly, to be regarded in an illustrative rather than a restrictive sense.

What is claimed is:

1. A method comprising:
   positioning a delivery device that provides vascular infusion or myocardial injection at a location in a vessel within the vasculature within a mammalian body;
   introducing by vascular infusion or myocardial injection to one of an infarct region and a perfused region of myocardium adjacent the infarct region an amount of a first treatment agent comprising a cellular component through the delivery device; and
   separately introducing by vascular infusion or myocardial injection to the other of the infarct region and the perfused region an amount of a second treatment agent disposed in a carrier particle through the delivery device, the second treatment agent selected from a group consisting of a growth factor, an inflammatory agent of nicotine or poly(methacrylic acid-co-methyl-methacrylate), and a homing factor having a property that will attract the cellular component;
   wherein introducing an amount of a second treatment agent disposed in a carrier particle comprises introducing a plurality of carrier particles, at least a portion of which comprise the amount of the second treatment agent, the carrier particles comprising a first group of carrier particles, at least one of the carrier particles of the first group having a diameter of from 5 μm to 30 μm to provide a first release rate and a second group of carrier particles, at least one of the carrier particles of the second group having a diameter between 30 µm and 80 µm to provide a second release rate different from the first release rate such that collectively a release rate of each of the plurality of microparticles defines a release rate gradient.

2. The method of claim 1, wherein introducing an amount of the first treatment agent comprises introducing to a perfused region of myocardium adjacent and separate from an infarct region.

3. The method of claim 2, wherein introducing an amount of the second treatment agent comprises introducing to the infarct region.

4. The method of claim 1, wherein the carrier particle comprises a microparticle.

5. The method of claim 1, wherein the first release rate is faster than the second release rate.

6. The method of claim 1, wherein the second treatment agent comprises a homing factor.

7. The method of claim 3, wherein introducing the second treatment agent comprises vascular infusing.

8. The method of claim 3, wherein introducing the amount of the second treatment agent comprises myocardial injecting.

9. The method of claim 4, wherein the microparticles comprise a minimally-immunogenic collagen.

10. The method of claim 4, wherein the microparticles comprise a hydrogel.

11. The method of claim 10, wherein the hydrogel comprises a modified alginate.

12. The method of claim 4, wherein the microparticles comprise an encapsulation polymer.

* * * * *